United States Patent
Cook et al.

(10) Patent No.: US 9,144,498 B2
(45) Date of Patent: Sep. 29, 2015

(54) MODULAR KNEE PROSTHESIS SYSTEM FOR USE WITH DIFFERENT LOAD REQUIREMENTS

(71) Applicant: DEPUY (IRELAND), Cork (IE)

(72) Inventors: Michael A. Cook, Claypool, IN (US); Filip Leszko, Winona Lake, IN (US); Aaron J Matyas, Fort Wayne, IN (US)

(73) Assignee: DEPUY (IRELAND), Cork (IE)

( * ) Notice: Subject to any disclaimer, the term of this patent is extended or adjusted under 35 U.S.C. 154(b) by 34 days.

(21) Appl. No.: 13/834,657

(22) Filed: Mar. 15, 2013

(65) Prior Publication Data
US 2014/0277527 A1 Sep. 18, 2014

(51) Int. Cl.
*A61F 2/38* (2006.01)
*A61F 2/30* (2006.01)

(52) U.S. Cl.
CPC . *A61F 2/38* (2013.01); *A61F 2/389* (2013.01); *A61F 2/3859* (2013.01); *A61F 2/30749* (2013.01); *A61F 2002/30332* (2013.01); *A61F 2002/30405* (2013.01)

(58) Field of Classification Search
CPC .................. A61F 2/389; A61F 2/3859; A61F 2002/30616; A61F 2002/30604; A61F 2220/0033; A61F 2220/0025
USPC ............................................ 623/20.15, 23.44
See application file for complete search history.

(56) References Cited

U.S. PATENT DOCUMENTS

| | | | |
|---|---|---|---|
| 5,782,921 A | 7/1998 | Colleran et al. | |
| 6,171,342 B1 | 1/2001 | O'Neil et al. | |
| 7,998,217 B1 * | 8/2011 | Brown | 623/20.15 |
| 8,366,782 B2 | 2/2013 | Wright | |
| 2004/0254646 A1 * | 12/2004 | Stone et al. | 623/23.15 |
| 2009/0088862 A1 | 4/2009 | Thomas et al. | |
| 2013/0204390 A1 * | 8/2013 | Podolsky | 623/22.42 |

* cited by examiner

*Primary Examiner* — Thomas J Sweet
*Assistant Examiner* — Brian Dukert (57) ABSTRACT

A modular orthopaedic implant system has first, second and third implant components. Two of the components have bores and the third component has a post. The third component can be assembled with either the first or second components with the post received in the respective bore of the other component. When assembled, the length of the post received within the bore of one of the components is greater than the length of the post received within the bore of the other component. The fatigue strength of the assembly with a greater length of the post received within the bore is greater, and this assembly can be used where such greater fatigue strength is needed and the other assembly can be used where a lesser fatigue strength is needed. Since the third component that is used in both assemblies may be the same, inventory may be reduced.

10 Claims, 4 Drawing Sheets

MODULAR KNEE PROSTHESIS SYSTEM FOR USE WITH DIFFERENT LOAD REQUIREMENTS

TECHNICAL FIELD

The present disclosure relates generally to prosthetic joints, and more particularly to a modular prosthetic knee joint system that includes components connected together with varying contact areas between the components.

BACKGROUND

The knee joint basically consists of the bone interface of the distal end of the femur and the proximal end of the tibia. Appearing to cover or at least partially protect this interface is the patella, which is a sesamoid bone within the tendon of the long muscle (quadriceps) on the front of the thigh. This tendon inserts into the tibial tuberosity and the posterior surface of the patella is smooth and glides over the femur.

The femur is configured with two knob like processes (the medial condyle and the lateral condyle) which are substantially smooth and which articulate with the medial plateau and the lateral plateau of the tibia, respectively. The plateaus of the tibia are substantially smooth and slightly cupped thereby providing a slight receptacle for receipt of the femoral condyles.

When the knee joint is damaged whether as a result of an accident or illness, a prosthetic replacement of the damaged joint may be necessary to relieve pain and to restore normal use to the joint. Typically the entire knee joint is replaced by means of a surgical procedure that involves removal of the surfaces of the corresponding damaged bones and replacement of these surfaces with prosthetic implants. This replacement of a native joint with a prosthetic joint is referred to as a primary total-knee arthroplasty.

On occasion, the primary knee prostheses fails. Failure can result from many causes, including wear, aseptic loosening, osteolysis, ligamentous instability, arthrofibrosis and patellofemoral complications. When the failure is debilitating, revision knee surgery may be necessary. In a revision, the primary knee prosthesis is removed and replaced with components of a revision prosthetic knee system.

Knee implant systems for both primary and revision applications are available from a variety of manufacturers, including DePuy Synthes Products, LLC of Warsaw, Ind. DePuy and others offer several different systems for both primary and revision applications. For example, DePuy Synthes Sales, Inc. offers the P.F.C. SIGMA® Knee System, the LCS® Total Knee System, and the S-ROM Modular Total Knee System. These orthopaedic knee systems includes several components, some appropriate for use in primary knee arthroplasty and some appropriate for use in revision surgery.

DePuy Synthes Sales, Inc. also offers other orthopaedic implant systems for other applications. One such system is the LPS System. The LPS System is provided for use in cases of severe trauma and disease. In such cases, the trauma or disease can lead to significant amounts of bone loss.

These systems include modular components, allowing the surgeon to construct an implant that meets the needs of the individual patient. Some combinations include modular stem extensions for use in conjunction with a distal femoral implant component, a proximal tibial implant component, or metaphyseal sleeves that may be used with such femoral and tibial implant components.

Although these prior knee implant systems have provided surgeons with great flexibility in meeting patient needs, and the modularity of these systems provides the opportunity to reduce the number of components needed in a surgical kit, these systems still require a substantial number of components.

In these assemblies of modular components, the fatigue strength of the components at their connections is important in ensuring the longevity of the assembly in use, and the characteristics of the connection components, and in particular, the dimensions of the connection components, are significant in ensuring that the assembly has an appropriate fatigue strength. However, the loading requirements for different assemblies may vary; for example, the loading requirements for the connection between a femoral stem connection may be greater than the loading requirements for a tibial stem connection. If the geometry of the connection of the tibial components satisfies the fatigue strength loading requirements for tibial loading, this same geometry may not satisfy the fatigue strength loading requirements for femoral loading. Moreover, if the connection includes a metaphyseal sleeve, the loading requirements may further differ. If the connections are optimized for the maximum anticipated loads, then the design may not meet other constraints; for example, design constraints for the tibial components may not allow for use of a connection that is optimum for the femoral components. Therefore, different components may be required for use on the femoral and tibial sides; for example, different stem configurations may need to be provided for use with the femoral and tibial components. Since multiple sizes of components are also required, duplicates of each size of stem may be required, substantially increasing the number of components in each set of implants provided to the surgeon.

Accordingly, a need exists for a modular prosthesis system that optimizes the fatigue strength of each modular connection while allowing for a more limited number of components required in each implant set provided to the surgeon.

SUMMARY

The present invention provides a modular knee implant system that allows for a single modular implant component to be selectively combined with two other implant components and to provide different fatigue strengths in each combination.

In one aspect, the present invention provides a modular orthopaedic implant system comprising a first, second and third implant component. The first implant component has an opening and a first bore defined by an internal surface; the first bore extends from the opening and has an axial length. The second implant component has an opening and a second bore defined by an internal surface; the second bore extends from the opening and has an axial length. The third implant component has a post at one end; the post has an outer surface and an axial length. The third implant component can be assembled with the first implant component by extending the post into and engaging the internal surface of the first bore. The third implant component has a fully engaged position defined by the maximum extent to which the post can extend into the first bore. The third implant component can be assembled with the second implant component by extending the post into and engaging the internal surface of the second bore. The third implant component has a fully engaged position defined by the maximum extent to which the post can extend into the second bore. When the third implant component is in the fully engaged position in the first bore of the first implant component, a first received length of the post is received in the first bore. When the third implant component is in the fully engaged position in the bore of the second implant component, a second received length of the post is received in the second bore. The first received length of the post is different from the second received length of the post.

In an illustrative embodiment, the internal surface of the first bore is tapered and has a maximum transverse dimension at the opening, a minimum transverse dimension at an end position spaced from the opening and an intermediate transverse width at a position between the opening and the end position. In the embodiment, the internal surface of the second bore is tapered and has a maximum transverse dimension at the opening, a minimum transverse dimension at an end position spaced from the opening and an intermediate transverse width at a position between the opening and the end position. Also in this embodiment, the outer surface of the post is tapered and has a frusto-conical shape, a minimum transverse width at an end of the post, a second transverse width at a position spaced axially from the end and an intermediate transverse width at a position between the end and the position of the second transverse width, the intermediate transverse width being greater than the minimum transverse width and less than the second transverse width. The axial length and transverse dimensions of the first bore of the first implant component and the axial length and transverse dimensions of the post of the third implant component allow for the outer surface of the post to frictionally lock with the tapered surface of the first bore at a first axial position along the post when in the fully engaged position. The axial length and transverse dimensions of the second bore of the second implant component and the axial length and transverse dimensions of the post of the third implant component allow for the outer surface of the post to frictionally lock with the tapered surface of the second bore at a second axial position along the post when in the fully engaged position. The first axial position is different from the second axial position.

In another illustrative embodiment, the axial length of the first bore is less than the axial length of the second bore. In a more particular embodiment, the maximum transverse dimension of the first bore is less than the maximum transverse dimension of the second bore.

In another illustrative embodiment, the first implant component and second implant component are selected from the group consisting of a distal femoral implant component and a proximal tibial implant component. In a more particular embodiment, the third implant component comprises a stem extension.

In another illustrative embodiment, the internal surface of the first bore is threaded, the internal surface of the second bore is threaded and the outer surface of the post is threaded.

In another illustrative embodiment, the first received length of the post comprises the entire axial length of the post and the second received length of the post comprises less than the entire axial length of the post.

In another aspect, the present invention provides a modular orthopaedic implant system comprising a first, second and third implant component. The first implant component has an opening and a first bore defined by a tapered wall; the first bore has an axial length, a maximum transverse dimension at the opening, a minimum transverse dimension at an end position spaced from the opening and an intermediate transverse width at a position between the opening and the end position. The second implant component has an opening and a second bore defined by a tapered wall; the second bore has an axial length, a maximum transverse dimension at the opening, a minimum transverse dimension at an end position spaced from the opening and an intermediate transverse width at a position between the opening and the end position. The third implant component has a post at one end; the post comprises a tapered outer surface having a frusto-conical shape, an axial length, a minimum transverse width at an end of the post, a second transverse width at a position spaced axially from the end and an intermediate transverse width at a position between the end and the position of the second transverse width. The intermediate transverse width of the post being greater than the minimum transverse width and less than the second transverse width. The axial length and transverse dimensions of the first bore of the first implant component and the axial length and transverse dimensions of the post of the third implant component allow for the outer surface of the post to frictionally lock with the tapered wall of the first bore at a first axial position along the post. The axial length and transverse dimensions of the second bore of the second implant component and the axial length and transverse dimensions of the post of the third implant component allow for the outer surface of the post to frictionally lock with the tapered wall of the second bore at a second axial position along the post. The first axial position is different from the second axial position.

In an illustrative embodiment, the axial length of the first bore is less than the axial length of the second bore.

In another illustrative embodiment, the maximum transverse dimension of the first bore is less than the maximum transverse dimension of the second bore.

In another illustrative embodiment, the taper angle of the bore of the first implant component is different from the taper angle of the bore of the second implant component.

In another illustrative embodiment, the first implant component and second implant component are selected from the group consisting of a distal femoral implant component and a proximal tibial implant component. In a more particular embodiment, the third implant component comprises a stem extension.

In another aspect, the present invention provides first, second and third implant components. The first implant component has an opening and a first bore defined by a threaded internal surface; the first bore extends from the opening and has an axial length. The second implant component has an opening and a second female bore defined by a threaded internal surface; the second bore extends from the opening and has an axial length. The third implant component has a post at one end; the post has a threaded outer surface and an axial length. The third implant component can be assembled with the first implant component by extending the threaded post into and engaging the internal threaded surface of the first bore. The third implant component has a fully engaged position defined by the maximum extent to which the post can extend into the first bore. The third implant component can be assembled with the second implant component by extending the threaded post into and engaging the threaded internal surface of the second bore. The third implant component has a fully engaged position defined by the maximum extent to which the post can extend into the second bore. When the third implant component is in the fully engaged position in the first bore of the first implant component, a first received length of the post is received in the first bore. When the third implant component is in the fully engaged position in the bore of the second implant component, a second received length of the post is received in the second bore. The first received length of the post is different from the second received length of the post.

In an illustrative embodiment, the first implant component and second implant component and selected from the group consisting of a distal femoral implant component and a proximal tibial implant component. In a more particular embodiment, the third implant component comprises a stem extension.

BRIEF DESCRIPTION OF THE DRAWINGS

The detailed description particularly refers to the accompanying figures in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Terms representing anatomical references, such as anterior and posterior, medial and lateral, proximal, distal, etcetera, may be used throughout the specification in reference to the orthopaedic implants described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

As used herein, "Morse taper" refers to locking tapers between mating components. Generally, Morse taper posts and bores have frusto-conical shapes, substantially the same taper angle and have complementary outer and inner diameters at some point along their length to allow for tight frictional engagement between the posts and the walls defining the bores. In embodiments employing Morse tapers, standard taper angles and standard surface finishes for such locking tapers may be used in the present invention.

Figure 1:
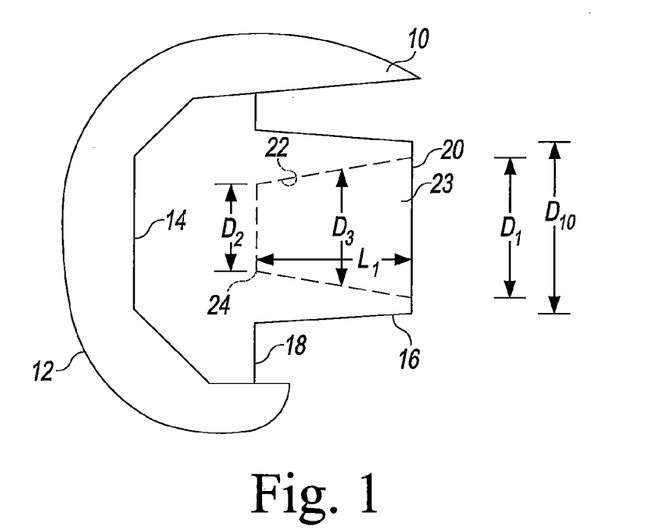
FIG. 1 is a side view of a distal femoral component of a modular knee prosthesis system.
Figures 2, 3:
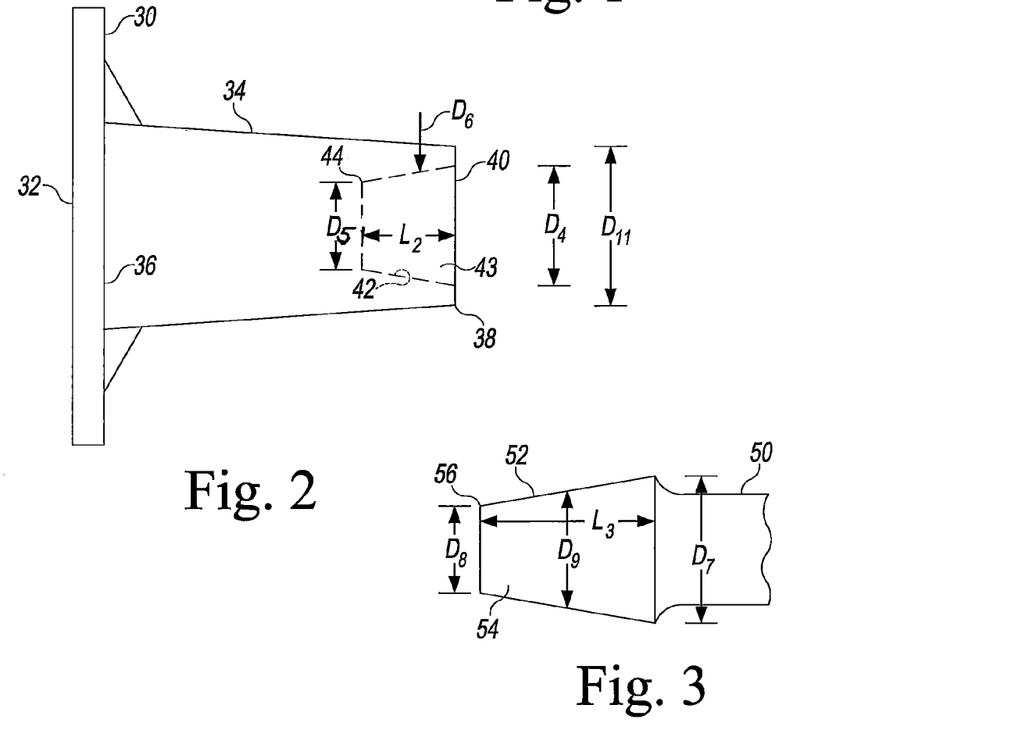
FIG. 2 is a side view of a proximal tibial component of a modular knee prosthesis system.
FIG. 3 is a side view of a portion of a stem component of a modular knee prosthesis system.

FIGS. 1-3 illustrate parts of a modular orthopaedic implant system embodying the principles of the present invention. The illustrated system is a modular knee implant system. Although the invention is described in terms of the illustrated modular knee implant system, it should be understood that the principles of the invention may be applied to other modular implant systems, such as modular hip, ankle and shoulder implant systems. It should also be understood that a typical implant system includes other components not illustrated, such as a tibial bearing insert and a patella implant component. Some systems may also include metaphyseal sleeves. It should also be understood that a typical implant kit provided to a surgeon would include multiple sizes of each of the components, to allow for the implants to be matched to the individual patient anatomy.

FIG. 1 illustrates an example of a distal femoral component 10 of a modular knee prosthesis system illustrating the principles of the present invention. The distal femoral component of the system includes a pair (medial and lateral) of distal curved convex condylar articular surfaces, one of such surfaces being shown at 12 in FIG. 1. The illustrated distal femoral component 10 also includes bone-contacting surfaces 14 opposite the articular surfaces 12. The illustrated component 10 includes an upstanding boss 16 extending proximally from an intercondylar box 18.

The upstanding boss 16 includes a proximal opening 20 at its proximal end, which may be circular in shape. An internal surface 22 extends distally from the proximal opening and defines a bore 23 of the femoral implant component 10. The internal surface 22 is tapered so that the first illustrated bore 23 defines a Morse taper bore having a frusto-conical shape. The bore has an axial length "$L_1$", a maximum transverse dimension (shown at "$D_1$" in FIG. 1) at the proximal opening 20, a minimum transverse dimension (shown at "$D_2$" in FIG. 1) at an end position 24 spaced from the opening 20 and an intermediate transverse dimension (shown at "$D_3$" in FIG. 1) between the opening 20 and the end position 24.

FIG. 2 illustrates an example of a proximal tibial component 30 of a modular knee prosthesis system illustrating the principles of the present invention. The proximal tibial component 30 of the system includes a proximal plateau 32 on which the bearing insert (not shown) is supported. A stem 34 extends distally from the bone-contacting surface 36 of the proximal plateau 32 to a distal end 38.

The tibial stem 34 includes a distal opening 40 at its distal end 38, which may be circular in shape. An internal surface 42 extends proximally from the distal opening and defines a bore 43 of the tibial implant component 30. The internal surface 42 is tapered so that the second illustrated bore 43 defines a Morse taper bore having a frusto-conical shape. The bore has an axial length "$L_2$", a maximum transverse dimension (shown at "$D_4$" in FIG. 2) at the distal opening 40, a minimum transverse dimension (shown at "$D_5$" in FIG. 2) at an end position 44 spaced from the opening 40 and an intermediate transverse dimension (shown at "$D_6$" in FIG. 2) between the opening 40 and the end position 44.

FIG. 3 illustrates an example of a portion of a stem extension component 50 of a modular knee prosthesis system illustrating the principles of the present invention. The illustrated stem extension 50 may be selectively assembled with either the distal femoral implant component 10 of FIG. 1 or the proximal tibial component 30 of FIG. 2. To make these assemblies, one end of the stem extension 50 comprises a post 52 with a tapered outer surface 54 having a frusto-conical shape so that the illustrated post 52 defines a Morse taper post. The post has an axial length "$L_3$", a maximum transverse dimension (shown at "$D_7$" in FIG. 3), a minimum transverse dimension (shown at "$D_8$" in FIG. 3) at an end position 56 and an intermediate transverse dimension (shown at "$D_9$" in FIG. 3) between the end 56 and the position corresponding with the maximum transverse dimension $D_7$.

Standard materials (e.g., titanium alloys and cobalt-chromium-molybdenum allows), finishes and tolerances for frictional locking implant components may be used for the tapered bores and post.

For the femoral component, $D_1 > D_3 > D_2$. For the tibial component, $D_4 > D_6 > D_5$. For the stem extension, $D_7 > D_9 > D_8$. In the illustrated modular system, the maximum transverse dimension $D_1$ and axial length $L_1$ of the femoral bore 23 are greater than the maximum transverse dimension $D_4$ and axial length $L_2$ of the tibial bore 43.

Figure 4:
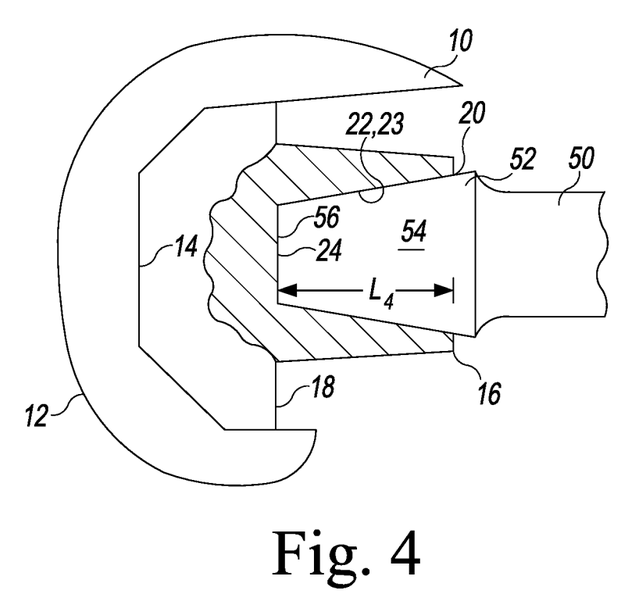
FIG. 4 is a view similar to FIG. 1, showing the distal femoral component assembled with the stem component of FIG. 3, with a portion of the distal femoral component shown in cross-section.

The stem extension 50 can be assembled with the distal femoral component 10 by extending the post 52 into and engaging the internal surface 22 of the first bore 23. The stem extension 50 has a fully engaged position defined by the maximum extent to which the post 52 can extend into the first bore 23. This fully engaged position is illustrated in FIG. 4. When the stem extension 50 is in the fully engaged position in the first bore 23 of the distal femoral component 10, a first received length of the post 52 is received in the first bore 23. This first received length is shown at $L_4$ in FIG. 4.

Figure 5:
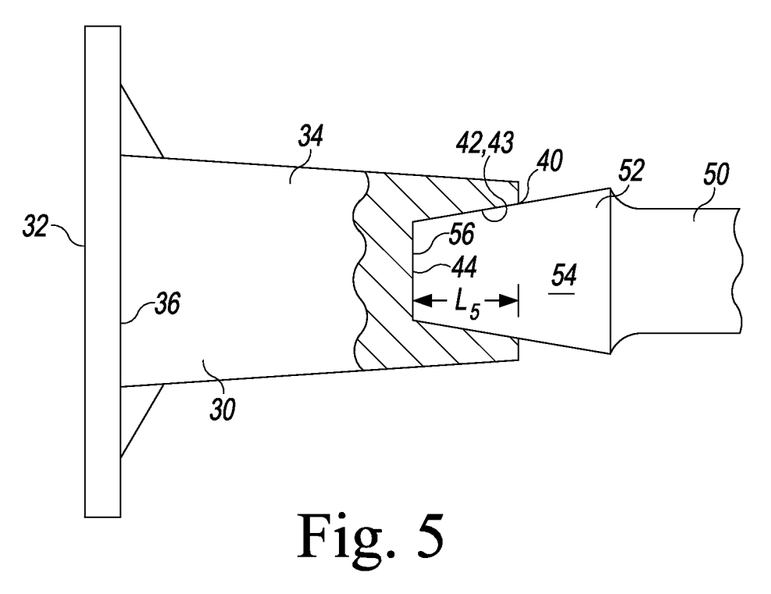
FIG. 5 is a view similar to FIG. 2, showing the proximal tibial component assembled with the stem component of FIG. 3, with a portion of the proximal tibial component shown in cross-section.

The same stem extension 50 can also be assembled with the proximal tibial implant component 30 by extending the post 52 into and engaging the internal surface 42 of the second bore 43. The stem extension 50 has a fully engaged position defined by the maximum extent to which the post 52 can extend into the second bore 43. This fully engaged position is illustrated in FIG. 5. When the stem extension 50 is in the fully engaged position in the bore 43 of the stem 34 of the proximal tibial implant component 30, a second received length of the post 52 is received in the second bore 43. This second received length is shown at $L_5$ in FIG. 5.

In the first illustrated embodiment, the end 56 of the post 52 extends substantially to the ends 24, 44 of the bores 23, 43 when the stem extension is fully engaged with the distal femoral component and proximal tibial component. Thus, in the first illustrated embodiment, the first received length $L_4$ of the post 52 corresponds substantially with the axial length $L_1$ of the first bore 23 and the second received length $L_5$ of the post 52 corresponds substantially with the axial length $L_2$ of the second bore 43. It should, however, be understood that $L_4$ may be less than $L_1$ and $L_5$ may be less than $L_2$; there will be clearance between the end of the male taper and the end of the female taper to account for tolerance stack-up and long-term taper subsidence.

The axial length $L_1$ and transverse dimensions $D_1$, $D_2$ and $D_3$ of the first bore 23 of the distal femoral implant component 10 and the axial length $L_3$ and transverse dimensions $D_7$, $D_8$ and $D_9$ of the post 52 of the stem extension 50 allow for the tapered outer surface 54 of the post 52 to frictionally lock with the tapered internal surface 22 of the first bore 23 at a first axial position along the post when in the fully engaged position.

The axial length $L_2$ and transverse dimensions $D_4$, $D_5$ and $D_6$ of the second bore 43 of the proximal tibial implant component 30 and the axial length $L_3$ and transverse dimensions $D_7$, $D_8$ and $D_9$ of the post 52 of the stem extension 50 of the third implant component allow for the tapered outer surface 54 of the post 52 to frictionally lock with the tapered internal surface 42 of the second bore 43 at a second axial position along the post 52 when in the fully engaged position.

As can be seen by comparing FIGS. 4 and 5, the first axial position is further from the end 56 of the post 52 than is the second axial position. Moreover, the first received length $L_4$ of the post 52 is greater than the second received length $L_5$ of the post 52. In both, the post 52 may frictionally engage the surfaces 22, 42 defining the bores 23, 43 along substantially the entire received lengths $L_4$ and $L_5$. The illustrated geometries may be dimensioned and the taper lock positions controlled to optimize the fatigue strength of both assemblies. This result can be accomplished without unnecessarily increasing the number of stem extension components that are needed in a set of modular implants, and without requiring the transverse dimension $D_{11}$ (see FIG. 2) of the distal end of the tibial stem 34 to be increased to match the transverse dimension $D_{10}$ of the proximal end of the boss 16.

To further optimize inventory control, multiple sizes of femoral components 10, tibial components 30 and stem extensions 50 may share common bore and post dimensions. For example, a larger size of distal femoral implant component may be provided in the kit having a bore substantially the same as bore 23 so that the same stem extension 50 can be used with multiple sizes of distal femoral implant components. Similarly, a larger size of proximal tibial implant component may be provided in the kit having a bore substantially the same as bore 43 so that the same stem extension 50 can be used with multiple sizes of proximal tibial implant components. And, a larger size of stem extension could be provided with a post of substantially the same dimensions as post 52 so that multiple sizes of stem extensions can be used with multiple sizes of distal femoral implant components and multiple sizes of proximal tibial implant components.

In the first illustrated embodiment, the axial length of the frictional lock between the post 52 and the surface 22 defining the bore 23 may extend substantially the first received length $L_4$; the axial length of the frictional lock between the post 52 and the surface 42 defining the bore 43 may extend substantially the second received length $L_5$. However, the axial lengths of the frictional locks between these components may be the same, as illustrated in the embodiment of FIGS. 6-7.

Figure 6:
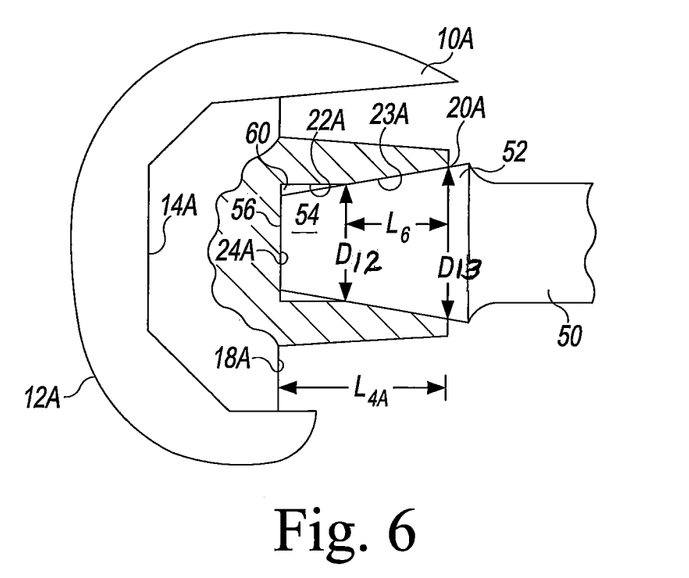
FIG. 6 is a view similar to FIG. 4, showing an alternative shape for the bore in the distal femoral component.
Figure 7:
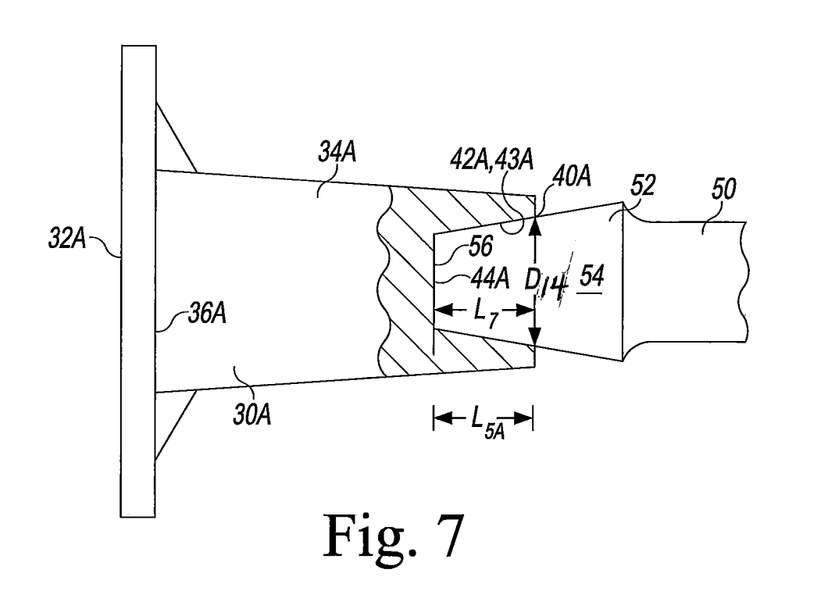
FIG. 7 is a view similar to FIG. 5, showing an alternative where the shape of the bore in the proximal tibial component is different from the shape of the bore in the distal femoral component of FIG. 6.

In the embodiment of FIGS. 6-7, parts similar to those described above for the first embodiment are labeled with the same reference numbers, followed by the letter "A". It should be understood that the above description of the distal femoral component 10 and proximal tibial component 30 apply as well to the distal femoral component 10A and proximal tibial component 30A unless distinguished in the following description.

In the embodiment of FIG. 6, the taper angle for the bore 23A of the distal femoral component 10A is different from the taper angle for the bore 43A of the proximal tibial component 30A but the same stem extension 50 shown in FIG. 3 is used with the components 10A and 30A. The result is that although there is some clearance (shown at 60 in FIG. 6) between the tapered outer surface 54 of the post 52 and the tapered internal surface 22A of the bore 23A, the surfaces 54, 22A of the post and the distal femoral component frictionally engage along axial length $L_6$ between transverse dimensions $D_{12}$ and $D_{13}$ (rather than along the entire received length $L_{4A}$). In FIG. 7, the surfaces 54, 42A frictionally engage along axial length $L_7$ between the ends 44A, 56 and transverse dimension $D_{14}$. Even though $L_6$ may equal $L_7$, the fatigue strength of the connection illustrated in FIG. 6 is higher, since $D_{13} > D_{14}$.

Although in all of FIGS. 1-7 the post is associated with the stem extension 50 and the bores 23, 43 are associated with the femoral and tibial implant components 10, 30, it should be understood that the principles of the present invention may be applied to constructs where posts are provided on the femoral and tibial components and the bore is provided on the stem extension.

Figure 8:
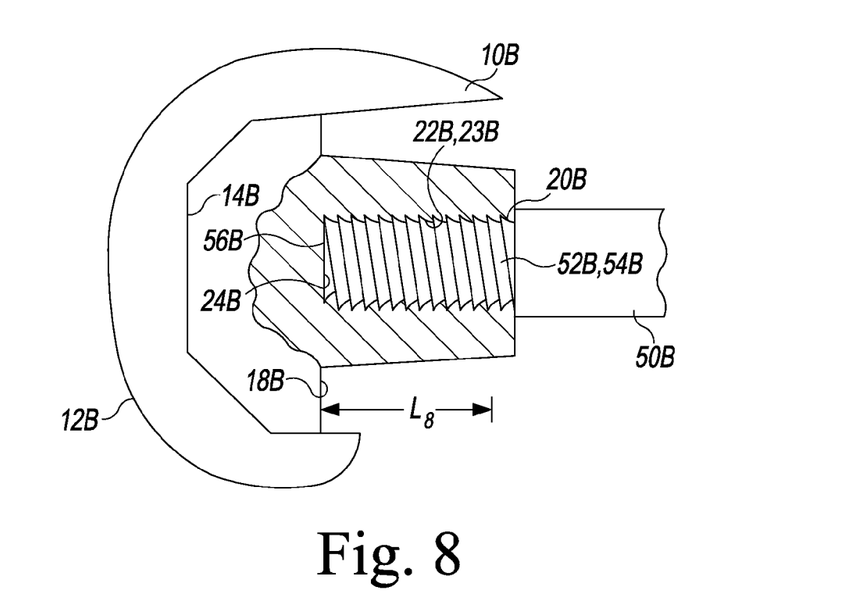
FIG. 8 is a view similar to FIG. 4, showing an alternative embodiment using a threaded bore and threaded post.
Figure 9:
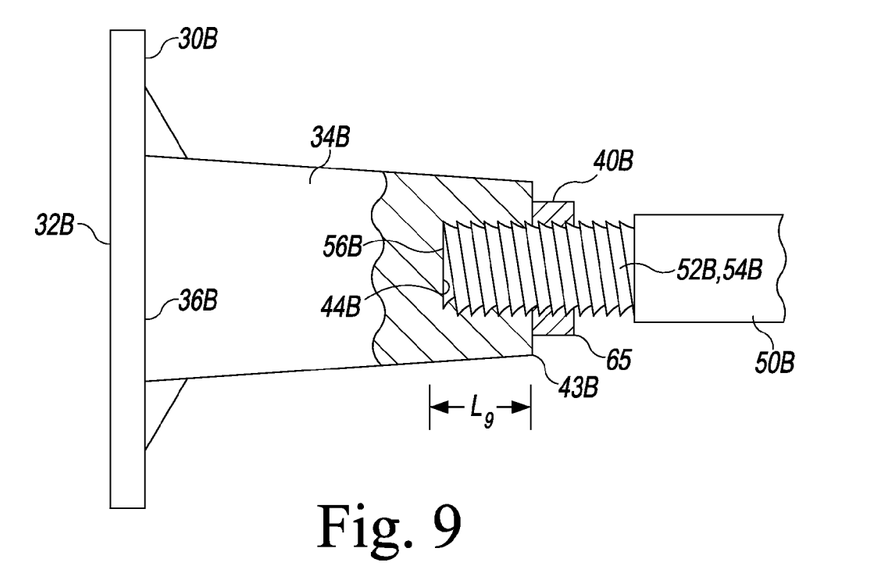
FIG. 9 is a view similar to FIG. 5, showing an alternative embodiment using a threaded bore and a threaded post.

A third alternative embodiment is illustrated in FIGS. 8-9. In the embodiment of FIGS. 8-9, parts similar to those described above for the first embodiment are labeled with the same reference numbers, followed by the letter "B". It should be understood that the above description of the distal femoral component 10, proximal tibial component 30 and stem component 50 apply as well to the distal femoral component 10B, proximal tibial component 30B and stem component 50B unless distinguished in the following description.

In the third embodiment, the stem component 50B has a threaded post 52B instead of a Morse taper post. The distal femoral implant component 10B has a threaded bore 23B instead of a Morse taper bore and the proximal tibial implant component 30B has a threaded bore 43B instead of a Morse taper bore. The thread size and pitch for the threaded portions of the components 10B, 30B, 50B may be the same, but as can be seen from a comparison of FIGS. 8 and 9, a greater length ($L_8$) of the threaded post 52B is received in the threaded bore 23B of the distal femoral implant component 10B than in the threaded bore 43B of the proximal tibial implant component 30B (the received length being shown at $L_9$). This embodiment should also provide greater fatigue strength at the femoral stem extension connection than at the tibial stem extension connection.

In the third embodiment, the threaded post 52B engages the threaded bore 23B along its entire received length $L_8$ and the threaded post 52B engages the threaded bore 43B along received length $L_9$. As shown in FIG. 9, it may be desirable to include a jam nut 65 as part of the assembly to strengthen the connection between the post 52B and the implant component 30B.

It should be appreciated that the principles of the present invention may also be applied to any modular orthopaedic implant system wherein components are connected through bores and posts.

Any of the above-described embodiments may also include standard elements for Morse taper and threaded connections between modular implant components. For example, air pressure relief passages (not illustrated) could be provided in any of these components.

It will be noted that alternative embodiments of each of the systems of the present disclosure may not include all of the features described yet still benefit from at least some of the advantages of such features. Those of ordinary skill in the art may readily devise their own implementations of a system that incorporates one or more of the features of the present disclosure and fall within the spirit and scope of the invention as defined by the appended claims.

We claim:

1. A modular orthopaedic implant system comprising:
    a first implant component having an exterior surface with an opening and a first bore defined by an internal surface, the first bore extending from the opening and having an axial length;
    a second implant component having an exterior surface with an opening and a second bore defined by an internal surface, the second bore extending from the opening and having an axial length;
    a third implant component having a post at one end, the post having a maximum outer diameter, a minimum outer diameter, an outer surface continuously tapering from the maximum outer diameter to the minimum outer diameter and an axial length between the maximum outer diameter and the minimum outer diameter;
    wherein:
    the third implant component can be assembled with the first implant component by extending the post into and engaging the internal surface of the first bore, the third implant component having a fully engaged position defined by the maximum extent to which the post can extend into the first bore;
    the third implant component can be assembled with the second implant component by extending the post into and engaging the internal surface of the second bore, the third implant component having a fully engaged position defined by the maximum extent to which the post can extend into the second bore;
    when the third implant component is in the fully engaged position in the first bore of the first implant component, a first received length of the post is received in the first bore;
    when the third implant component is in the fully engaged position in the bore of the second implant component, a second received length of the post is received in the second bore and a portion of the axial length of the post is exposed outside of the second bore so that a portion of the tapered outer surface of the post is on each side of the exterior surface of the second implant component; and
    the first received length of the post is different from the second received length of the post.

2. The modular orthopaedic implant system of claim 1 wherein:
    the internal surface of the first bore is tapered and has a maximum transverse dimension at the opening, a minimum transverse dimension at an end position spaced from the opening and an intermediate transverse width at a position between the opening and the end position;
    the internal surface of the second bore is tapered and has a maximum transverse dimension at the opening, a minimum transverse dimension at an end position spaced from the opening and an intermediate transverse width at a position between the opening and the end position;
    the outer surface of the post is tapered and has a frusto-conical shape, a minimum transverse width at an end of the post, a second transverse width at a position spaced axially from the end and an intermediate transverse width at a position between the end and the position of the second transverse width, the intermediate transverse width being greater than the minimum transverse width and less than the second transverse width;
    the axial length and transverse dimensions of the first bore of the first implant component and the axial length and transverse dimensions of the post of the third implant component allow for the outer surface of the post to frictionally lock with the tapered surface of the first bore at a first axial position along the post when in the fully engaged position;
    the axial length and transverse dimensions of the second bore of the second implant component and the axial length and transverse dimensions of the post of the third implant component allow for the outer surface of the post to frictionally lock with the tapered surface of the second bore at a second axial position along the post when in the fully engaged position; and
    the first axial position is different from the second axial position.

3. The modular orthopaedic implant system of claim 1 wherein the axial length of the second bore is less than the axial length of the first bore.

4. The modular orthopaedic implant system of claim 2 wherein the maximum transverse dimension of the first bore is less than the maximum transverse dimension of the second bore.

5. The modular orthopaedic implant system of claim 1 wherein the first implant component and second implant component are selected from the group consisting of a distal femoral implant component and a proximal tibial implant component.

6. The modular orthopaedic implant system of claim 5 wherein the third implant component comprises a stem extension.

7. The modular orthopaedic implant system of claim 1 wherein the outer surface of the post has a frusto-conical shape and wherein the first received length of the post comprises the entire axial length of the frusto-conically shaped post and the second received length of the post comprises less than the entire axial length of the frusto-conically shaped post.

8. A modular orthopaedic implant system comprising:
- a first implant component having an exterior surface with an opening and a first bore defined by a threaded internal surface, the first bore extending from the opening and having an axial length;
- a second implant component having an exterior surface with an opening and a second female bore defined by a threaded internal surface, the second bore extending from the opening and having an axial length;
- a third implant component having a post at one end, the post having a threaded outer surface and an axial length;

wherein:
the third implant component can be assembled with the first implant component by extending the threaded post into and engaging the threaded internal surface of the first bore, the third implant component having a fully engaged position defined by the maximum extent to which the post can extend into the first bore;

the third implant component can be assembled with the second implant component by extending the threaded post into and engaging the threaded internal surface of the second bore, the third implant component having a fully engaged position defined by the maximum extent to which the post can extend into the second bore;

when the third implant component is in the fully engaged position in the first bore of the first implant component, a first received length of the post is received in the first bore;

when the third implant component is in the fully engaged position in the bore of the second implant component, a second received length of the post is received in the second bore and a portion of the axial length of the post is exposed outside of the second bore so that a portion of the threaded outer surface of the post is on each side of the exterior surface of the second implant component; and the first received length of the post is different from the second received length of the post.

9. The modular orthopaedic implant system of claim 8 wherein the first implant component and second implant component and selected from the group consisting of a distal femoral implant component and a proximal tibial implant component.

10. The modular orthopaedic implant system of claim 9 wherein the third implant component comprises a stem extension.

\* \* \* \* \*